United States Patent [19]

Hucul et al.

[11] Patent Number: 4,743,705

[45] Date of Patent: May 10, 1988

[54] PREPARATION OF ACRYLATE ESTERS

[75] Inventors: Dennis A. Hucul; Kathryn A. Eickholt, both of Midland, Mich.

[73] Assignee: The Dow Chemical Company, Midland, Mich.

[21] Appl. No.: 839,314

[22] Filed: Mar. 13, 1986

Related U.S. Application Data

[63] Continuation of Ser. No. 636,055, Jul. 30, 1984, abandoned.

[51] Int. Cl.$^4$ .............................................. C07C 67/36
[52] U.S. Cl. ..................................... 560/207; 560/206
[58] Field of Search .............................. 560/206, 207; 260/544 A

[56] References Cited

U.S. PATENT DOCUMENTS

| | | | |
|---|---|---|---|
| 3,040,090 | 6/1962 | Alderson et al. | 560/175 |
| 3,116,306 | 12/1963 | Heck | 260/410.9 |
| 3,454,632 | 7/1969 | Mador et al. | 260/544 |
| 3,457,299 | 7/1969 | Closson et al. | 560/207 |
| 3,468,947 | 9/1969 | Scheben et al. | 260/544 |
| 3,626,005 | 12/1971 | Scheben et al. | 260/544 A |
| 3,636,082 | 1/1972 | Knowles | 560/97 |
| 3,772,384 | 11/1973 | Knowles | 560/105 |
| 3,819,669 | 6/1974 | Knifton | 260/410.9 R |
| 3,960,932 | 6/1976 | Heck | 560/144 |
| 3,988,358 | 10/1976 | Heck | 260/465 D |
| 3,991,101 | 11/1976 | Knifton | 560/207 |
| 4,128,554 | 12/1978 | Heck | 546/317 |
| 4,313,893 | 2/1982 | Pess et al. | 560/233 |
| 4,447,640 | 5/1984 | Eickholt | 560/207 |
| 4,480,121 | 10/1984 | Klun et al. | 560/206 |

FOREIGN PATENT DOCUMENTS 1091042 11/1967 United Kingdom .

OTHER PUBLICATIONS

Scholten, Journal of Catalysis, vol. 1, pp. 85–92 (1962).
Aben, Journal of Catalysis, 10, pp. 224–229, (1968).
Emmett, "Catalysis", vol. 1, pp. 315–352, (1954).
Scheben, John A. et al., "Synthesis by Carbon Monoxide Insertion at Carbon–Chlorine Bonds", pp. 181–201 of *Catalysis in Organic Synthesis* (1976), P. Rylonder and H. Greenfield, Editors, Academic Press, Publ.
J. Tsuji et al., *Tetrahedron Letters* (1963), pp. 1061–1064.

Primary Examiner—Michael L. Shippen

[57] ABSTRACT

The invention is a vapor phase process for the preparation of an a-substituted acrylate ester which comprises contacting a haloalkene, wherein the halogen is substituted on an olefinic carbon atom which is further substituted with a $C_{1-10}$ alkyl, $C_{3-10}$ cycloalkyl, $C_{6-10}$ aryl, $C_{7-10}$ alkaryl, $C_{7-10}$ aralkyl, cyano, trihalomethyl group, with an alcohol or an ether, and carbon monoxide in the presence of a heterogeneous catalyst which comprises palladium, platinum, nickel, ruthenium or rhodium, on a support, under conditions such that an a-substituted acrylate ester and a hydrocarbyl halide is prepared wherein the catalyst productivity is 0.06 g of product per gram of catalyst per hour or greater.

25 Claims, No Drawings

PREPARATION OF ACRYLATE ESTERS

CROSS-REFERENCE TO RELATED APPLICATION

This is a continuation of Ser. No. 636,055, filed July 30, 1984, now abandoned, which is hereby incorporated by reference.

BACKGROUND OF THE INVENTION

This invention relates to a novel process for the preparation of acrylate esters. More specifically, the invention relates to a vapor phase carbonylation of haloalkenes using heterogeneous catalysts to prepare acrylate esters.

One such acrylate ester is methylmethacrylate which is prepared commercially from acetone which is treated with HCN to give 2-cyano-2-propanol which is then treated with 98 percent sulfuric acid to give a salt of propene-2-amide and sulfuric acid. The salt is then reacted with methanol to prepare methylmethacrylate and ammonium sulfate. This process requires a large purification scheme and the use of sulfuric acid and hydrogen cyanide.

Heck, U.S. Pat. No. 3,988,358, discloses the preparation of alpha-unsaturated carboxylic esters have been prepared from olefinic halides, wherein the olefinic halides are contacted with carbon monoxide and an alcohol, phenol or polyglycol in the presence of an organic halide of a Group VIII metal catalyst. The Group VIII metal catalyst is added as finely divided palladium metal wherein the organic halide is an organic iodide or in the salt form to the reaction solution. It is further taught that the catalytic species is $RPdL_2X$ wherein R is aryl, heterocyclic, vinylic, ethynylic or benzylic or substituted derivatives thereof; L is a coordinating group such as triphenyl phosphine; X is Cl, Br or I; and n is 2, 3 or 4. It is further taught that the use of tertiary amines is usually necessary to make the reaction catalytic in palladium. This homogeneous process has a significant disadvantage in that the products are very difficult to recover, furthermore, recovery of the catalyst is also difficult.

Closson et al., U.S. Pat. No. 3,457,299, disclose a process for preparing unsaturated carboxylic acids by reacting a halogenated olefin and carbon monoxide, using as a catalyst rhodium, iridium, platinum, palladium, osmium, or ruthenium metal, or mixtures thereof. The halogenated olefin (1) must be stable to the reaction conditions, (2) must have the basic structure

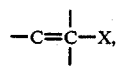

and (3) cannot be substituted with a group which retards or hinders the carbonylation. Preferred halogenated olefins are those with the structure

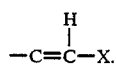

It is taught that the by-product is

HX
[HCl].

The reaction conditions used include pressures of 50 psi to 10,000 psi, with a highly preferred range of 2,000 psi to 5,000 psi, and temperatures from 250° C. to the decomposition temperature of the halogenated olefin. This process suffers from significant problems, specifically the catalyst demonstrates low conversions and relatively short lifetimes under the reaction conditions taught.

Scheben et al., U.S. Pat. No. 3,626,005, disclose the formation of unsaturated acid halides by the reaction of a haloalkene with carbon monoxide. It is further taught that alcohols can be used as diluents. The acid halide is recovered as the corresponding ester when alcohols are used as diluents. Alternatively, the recovered acid halide can be converted to an ester by contacting it with an alcohol. This process suffers from the problem that the productivity of the catalysts is low.

Scheben et al., *Catalysis in Organic Synthesis*, (5th Conf.), p. 181 (1975), teach that the reaction of 2-chloropropene with carbon monoxide in the presence of a heterogeneous palladium on alumina catalyst results in the transposition of the chlorine atom to the saturated carbon atom, and the formation of 3-butenoyl chloride as the product. It is further taught that 2-chloropropene isomerizes to allyl chloride in the presence of palladium catalysts.

The hereinbefore described carbonylation processes suffer from several problems. First, the homogeneous process creates significant problems in the recovery of both the catalyst and the product. The catalyst lifetimes in the processes described hereinbefore are very short. These processes demonstrate a low selectivity for the desired carboxylic acid esters. Furthermore, the productivity of the catalysts is too low to justify commercialization.

What is needed is a heterogeneous catalyst for the carbonylation of haloalkenes to prepare carboxylic acid esters wherein the catalyst demonstrates extended lifetimes, with good selectivities towards the desired carboxylic acid esters and the catalyst demonstrates a high productivity.

SUMMARY OF THE INVENTION

The invention is a vapor phase process for the preparation of an α-substituted acrylate ester which comprises contacting (a) a haloalkene, wherein the halogen is substituted on an olefinic carbon atom which is further substituted with a $C_{1-10}$ alkyl, $C_{3-10}$ cycloalkyl, $C_{6-10}$ aryl, $C_{7-10}$ alkaryl, $C_{7-10}$ aralkyl, cyano, or trihalomethyl group; (b) an alcohol or an ether; and (c) carbon monoxide in the presence of a heterogeneous catalyst which comprises palladium, platinum, nickel, ruthenium or rhodium, on a support under conditions such that an α-substituted acrylate ester and a hydrocarbyl halide is prepared wherein the catalyst productivity is 0.06 g of product per gram of catalyst per hour or greater.

The process of this invention has several advantages. First, the use of a heterogeneous catalyst in the vapor phase allows easy recovery of the products and does not present a problem in the recovery of the catalyst as in a homogeneous process. The catalyst used demonstrates surprisingly high selectivities for the α-substituted acrylate esters and high productivities over extended periods of time.

DETAILED DESCRIPTION OF THE INVENTION

This invention relates to a process for the preparation of α-substituted acrylate esters by the carbonylation of a haloalkene with carbon monoxide and the esterification with alcohol or ether in the vapor phase over a heterogeneous catalyst.

The haloalkenes useful in this invention include any halogenated olefinic compound wherein the halogen is substituted on an olefinic carbon atom, wherein such carbon atom is further substituted with a $C_{1-10}$ alkyl, $C_{3-10}$ cycloalkyl, $C_{6-10}$ aryl, $C_{7-10}$ alkaryl, $C_{7-10}$ aralkyl, cyano, or trihalomethyl group, and which is vaporizable under the reaction conditions. Olefinic carbon atom means herein a carbon atom which is doubly bonded to another carbon atom. Haloalkenes useful in this invention include those which correspond to the formula

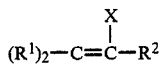

wherein $R^1$ is hydrogen $C_{7-10}$ aryl, $C_{1-10}$ alkyl, $C_{3-10}$ cycloalkyl, $C_{7-10}$ alkaryl, $C_{7-10}$ aralkyl, substituted $C_{1-10}$ alkyl, substituted $C_{6-10}$ aryl, substituted $C_{3-10}$ cycloalkyl, substituted $C_{7-10}$ alkaryl or substituted $C_{7-10}$ aralkyl, wherein the substituent is a nitro, cyano, carbonyloxyhydrocarbyl, formyl, amino, hydroxyl, amido or halo group;

$R^2$ is $C_{1-10}$ alkyl, $C_{3-10}$ cycloalkyl, $C_{6-10}$ aryl, $C_{7-10}$ alkaryl, $C_{7-10}$ aralkyl, cyano or trihalomethyl; and X is halogen.

Examples of preferred haloalkenes useful in this invention include 2-chloropropene, 2-bromopropene, 2-chlorobutene, 2-bromobutene, 2-chloropentene, 3-chloropentene, 2-bromopentene, 3-bromopentene, 2-chlorohexene, 3-chlorohexene, 2-bromohexene, 3-bromohexene, and the like. More preferred haloalkenes include 2-chloropropene, 2-chlorobutene, 2-chloropentene, and 2-chlorohexene. A most preferred haloalkene is 2-chloropropene.

Alcohols useful in this invention include those which are vaporizable under reaction conditions and which will react under the reaction conditions to esterify the carbonylated haloalkene so as to prepare an α-substituted acrylate ester. Preferred alcohols include those which correspond to the formula, $R^3OH$, wherein $R^3$ is $C_{1-10}$ alkyl, $C_{3-10}$ cycloalkyl, $C_{6-10}$ aryl, $C_{7-10}$ alkaryl, or $C_{7-10}$ aralkyl. Examples of alcohols useful in this invention include methanol, ethanol, propanol, butanol, hexanol, heptanol, octanol, nonanol, decanol, cyclopropanol, cyclobutanol, cyclopentanol, cyclohexanol, cycloheptanol, cyclooctanol, phenol, benzyl alcohol, and the like. Preferred alcohols are methanol, ethanol, propanol, butanol, and pentanol. A most preferred alcohol is methanol.

Ethers useful in this invention include those which are vaporizable under reaction conditions and which will react under the reaction conditions to esterify the carbonylated haloalkene so as to prepare an α-substituted acrylate ester. Among classes of ethers useful in this invention are the dihydrocarbyl ethers and cyclic ethers. Preferred dihydrocarbyl ethers include those which correspond to the formula $R^3-O-R^3$ wherein $R^3$ is as defined hereinbefore. Examples of dihydrocarbyl ethers useful in this invention are dimethyl ether, diethyl ether, dipropyl ether, dibutyl ether, dipentyl ether, diphenyl ether, dibenzyl ether and the like. Preferred ethers are dimethyl ether, diethyl ether and dipropyl ether; with dimethyl ether being most preferred. Unsymmetrical dihydrocarbyl ethers such as methyl ethyl ether, can be used in this invention although the symmetrical ethers are preferred. Preferable cyclic ethers useful in this process include those which correspond to the formula

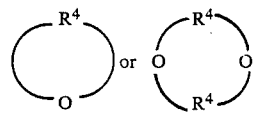

wherein $R^4$ is a hydrocarbylene radical. The dihydrocarbyl ethers are preferred over the cyclic ethers. Cyclic ethers useful in this invention include dioxane, tetrahydrofuran and the like.

The product of this invention is an acrylate ester. Preferred α-substituted acrylate esters include those which correspond to the formula

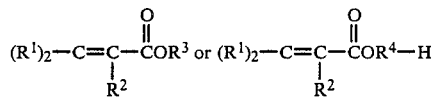

wherein $R^1$, $R^2$, $R^3$ and $R^4$ are as hereinbefore defined.

Examples of acrylate esters prepared by this process include methyl methacrylate, methyl 2-methyl-2-butenoate, methyl 2-methyl-2-pentenoate, ethyl methacrylate, ethyl 2-methyl-2-butenoate, ethyl 2-methyl-2-pentenoate, propyl methacrylate, propyl 2-methyl-2-butenoate, propyl 2-methyl-2-pentenoate, butyl methacrylate, butyl 2-methyl-2-butenoate, butyl 2-methyl-2-pentenoate, pentyl methacrylate, pentyl 2-methyl-2-butenoate, and pentyl 2-methyl-pentenoate. Preferred acrylate esters include methyl methacrylate, ethyl methacrylate, propyl methacrylate, butyl methacrylate, and pentyl methacrylate, more preferred acrylate esters include methyl methacrylate, ethyl methacrylate, and propyl methacrylate, with methyl methacrylate being most preferred.

A co-product of this invention is a hydrocarbyl halide. This halide is the reaction product of an alcohol or an ether and the halogen abstracted from the haloalkene during the carbonylation and esterification process of this invention. The excess alcohol or ether functions as the halogen acceptor for this reaction thereby reducing the concentration of hydrogen halide in the reactor and preventing corrosion. Furthermore, the preparation of an alkyl halide allows the recovery of the halogen in a valuable form. Hydrocarbyl halides prepared in this invention include those which correspond to the formula, $R^3-X$ or $R^4Y-X$, wherein $R^3$ and $R^4$ are as hereinbefore defined.

Tertiary amines may be used as hydrogen halide acceptors. When tertiary amines are used as acid acceptors, by-products of the process are the quaternary ammonium halides. The use of excess alcohols or ethers to serve as the halogen acceptor is preferred over the use of the teriary amines in this invention.

Examples of haloalkanes prepared by this process include chloromethane, chloroethane, chloropropane, chlorobutane, chloropentane, chlorohexane, chloroheptane, chlorooctane, chlorononane, chlorodecane, chlorocyclopropane, chlorocyclobutane, chlorocyclopentane, chlorocyclohexane, chlorobenzene, chloromethylbenzene, bromomethane, bromoethane, bromopropane, bromobutane, bromopentane, bromohexane, bromoheptane, bromooctane, bromononane, bromodecane, bromocyclopropane, bromocyclobutane, bromocyclopentane, bromocyclohexane, bromobenzene, and bromomethylbenzene. Examples of more preferred haloalkanes include chloromethane, chloroethane, chloropropane, chlorobutane, chloropentane, chlorohexane, chloroheptane, chlorooctane, chlorononane, chlorodecane, chlorocyclopropane, chlorocyclobutane, chlorocyclopentane, chlorocyclohexane, chlorobenzene, and chloromethylbenzene. Even more preferred haloalkanes include chloromethane, chloroethane, chloropropane, chlorobutane and chloropentane, with chloromethane being most preferred.

In the process of this invention, the haloalkene starting material is carbonylated by the insertion of carbon monoxide onto an olefinic carbon atom, and the carbon atom on the carbon monoxide moiety inserted is transesterified with the alcohol or ether. This process can be best illustrated by the following equations,

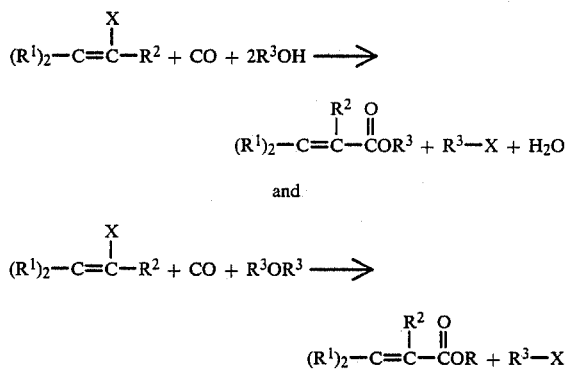

wherein $R^1$, $R^2$, $R^3$, and X are as hereinbefore defined.

In the hereinbefore defined formulas, $R^1$ is preferably hydrogen or $C_{1-10}$ alkyl. $R^1$ is more preferably hydrogen or $C_{1-5}$ alkyl and most preferably hydrogen. $R^2$ is preferably [hydrogen or] $C_{1-10}$ alkyl. $R^2$ is more preferably $C_{1-5}$ alkyl and most preferably methyl. $R^3$ is preferably $C_{1-10}$ alkyl. $R^3$ is more preferably $C_{1-5}$ alkyl and most preferably methyl. $R^4$ is preferably $C_{2-10}$ alkylene, and more preferably $C_{2-5}$ alkylene. X is preferably chlorine or bromine and most preferably chlorine.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

The choice of catalyst is critical to the achievement of high selectivities with high productivities and extended catalyst lifetimes. The catalysts useful in this invention are palladium, platinum, rhodium ruthenium, nickel or mixtures thereof on a support. Preferred catalysts are palladium or nickel on a support, with palladium on a support being most preferred.

The catalyst comprises a support with a sufficient amount of one of the hereinbefore described metals loaded thereon to give the desired catalyst productivity for the claimed process. The catalyst preferably comprises a support with between about 0.1 and 10 percent by weight of the hereinbefore described metal, more preferably between about 1 and 10 percent by weight, and most preferably between about 3 and 7 percent.

The catalysts of this invention are prepared by incipient wetness techniques, which are well-known in the art. In particular, a salt of the metals described hereinbefore is dissolved in water or an aromatic hydrocarbon and thereafter contacted with the particular support. Examples of salts which can be used include metal acetates, metal halides, metal nitrates, and the like.

A particularly preferred catalyst comprises palladium deposited onto a shaped γ-alumina support. Suitable γ-alumina supports are extrudates, pellets and other shaped articles of γ-alumina having a volume from about $1 \times 10^{-9}$ m$^3$ to about $2 \times 10^{-5}$ m$^3$, a surface area from about 10 m$^2$/g to about 350 m$^2$/g and more preferably from about 100 m$^2$/g to about 300 m$^2$/g, crush strength from about 1 lb/in$^2$ (703 kg/m$^2$) to about 1000 lb/in$^2$ ($7.03 \times 10^5$ kg/m$^2$) and containing about 3.0 to about 10.0 percent palladium based on total catalyst weight and a palladium dispersion from about 50 percent to about 95 percent.

The above-described highly dispersed, highly loaded, supported palladium on γ-alumina catalysts are prepared by contacting at an elevated temperature a previously prepared γ-alumina substrate and an aqueous hydrochloric acid solution of a palladium salt having a pH of 3.0 or less. Preferably, the substrate is heated to a temperature from about 75° C. to about 150° C. and the aqueous hydrochloric acid solution is heated to a temperature of from about 50° C. to about 95° C. at the time the support and solution are contacted. Only sufficient solution so as to result in incipient wetness of the substrate is employed. Accordingly, the volume and metal concentration of the aqueous solution are adjusted to provide sufficient metal loadings and sufficient volume of liquid to completely wet the alumina substrate, but not provide more liquid than can be absorbed by the alumina substrate. Preferably, the aqueous solution has a pH of 2.0 or less.

After impregnation with the palladium solution, the catalyst is dried in flowing air as elevated temperatures up to about 300° C. for several hours. Reduction may then occur employing hydrogen under the temperatures and conditions described hereinafter.

Supports useful in this invention include any support which is capable of withstanding the reaction conditions and has structural integrity. Preferred supports include alumina, activated carbon, silica, aluminosilicate zeolitic molecular sieves, titanium oxide, niobium oxide, lanthanum oxide, thorium oxide, or silicon carbide. More preferred supports include alumina, activated carbon, silica, or aluminosilicate zeolitic molecular sieves. Even more preferred supports include alumina, activated carbon or silica. The most preferred support is alumina.

Critical to obtaining a catalyst with high selectivities, high productivities and extended catalyst lifetimes is the process for the activation of the catalyst. The catalyst is activated by passing hydrogen gas over the impregnated catalytic support at a temperature of between about 150° C. and 350° C., for a period of time to reduce a significant amount of the metal salt impregnated on the support. Preferably, the hydrogen gas is passed over the support at a temperature of between about 225° C. and 300° C., with between about 240° C. and 280° C. being most preferred. It is preferable to flow hydrogen gas over the catalyst for a time period of between about 1 and 10 hours.

It is believed that during the activation procedure the metal is reduced to the zero valence state, which is believed to be the catalytic species.

In general, the support is impregnated with a sufficient amount of metal so as to create a catalyst which is active under the reaction conditions. The amount of active metal on the carrier can be between about 0.01 and 99 percent by weight of the support. Preferably, the catalyst contains between about 0.1 and 10 percent by weight of active metal. Even more preferably, the catalyst contains between about 1 and 10 percent by weight of the active metal, with between about 3 and 7 percent by weight of the active metal on the catalyst being most preferred.

It has been discovered that the presence of an alcohol or ether in the reactants results in significant increases in the productivity of the catalyst for the α-substituted acrylate ester. The mole ratio of the alcohol to the haloalkene in the feed composition has a significant effect on the productivities, conversions and selectivities. The productivities, conversions and selectivities are enhanced as the equivalent ratio of alcohol or ether to haloalkene increases from 1:1 to 2:1, at 2:1 the productivities, conversions and selectivities are optimized. The ratio of alcohol or ether to olefin can be any ratio which gives a desired conversion and selectivity. Preferably, the equivalent ratio of alcohol or ether to haloalkene is 1.5:1 or above. More preferably the alcohol or ether to haloalkene ratio is 2.0:1 or greater. An equivalent with respect to the alcohol or ether, refers herein to that amount of alcohol or ether which provides one mole of hydrocarbyl radicals. In particular, one mole of a dihydrocarbyl ether provides two equivalents of hydrocarbyl radicals, while one mole of an alcohol provides one equivalent of hydrocarbyl radicals.

At least a stoichiometric ratio of carbon monoxide to haloalkene is needed for this process to give good selectivities and conversions.

The temperature used for this process has a significant effect on the conversions, selectivities, catalyst productivity and catalyst lifetime. In practice, any temperature at which the desired conversions, selectivities, productivity, and catalyst lifetime are achieved can be used. Preferable reaction temperatures are between about 125° C. and 250° C. with 170° C. to 240° C. being more preferred. In general, above 250° C. the rate of reaction significantly decreases. Below 125° C., the reaction rate is extremely slow.

The reaction pressure also has a significant effect on the selectivities, conversions, catalyst productivity and catalyst lifetime. Any reaction pressure which gives the desired selectivities, conversions, catalyst productivity and catalyst lifetime can be used. Preferred pressures are between about 100 and 800 psi, with between about 300 and 600 psi being most preferred. Above 800 psi the rate of reaction drops dramatically and below 100 psi the selectivity of the reaction is very poor.

The flow rates over the catalyst can be any flow rate which gives the desired conversions and selectivities. In practice, the flow rate of carbon monoxide is between about 15 gas volumes of carbon monoxide per volume of catalyst per hour and 1500 gas volumes of carbon monoxide per volume of catalyst per hour. Preferably, the flow rate is between about 100 and 200 gas volumes of carbon monoxide per volume of catalyst per hour.

It is preferable that the alcohol or ether and haloalkene be vaporized by preheating before contacting them with the carbon monoxide in the presence of the catalyst. The combined alcohol or ether and haloalkene feed to the preheater is preferably between about 0.1 and 10 liquid volumes per volume of catalyst per hour. More preferably the feed rate is between about 0.5 and 1.5 liquid volumes of haloalkene and alcohol or ether per volume of catalyst per hour.

This process can be performed in a batch or continuous mode. Furthermore, the catalyst can be used as a fixed bed catalyst or in a fluid bed. It is preferred to use a continuous mode with a fixed bed catalyst.

In one preferred embodiment, methylmethacrylate is prepared by contacting 2-chloropropene, methanol, or dimethyl ether, and carbon monoxide in the vapor phase over a catalyst which comprises palladium on alumina wherein the concentration of palladium on the alumina is between about 1 and 7 percent by weight. In this embodiment, the catalyst is prepared by impregnating palladium chloride onto the alumina support. The catalyst is activated by passing hydrogen gas over the palladium chloride on alumina support at a temperature of between about 240° C. and 280° C. for a period of between 1 and 3 hours. In this embodiment, the contacting of the reactants takes place at between about 170° C. and 240° C. under a pressure of 300 to 600 psi.

The process of this invention results in a process for the preparation of acrylate esters wherein the catalyst exhibits long lifetimes, with good productivities and selectivities. The process of this invention results in catalyst productivities of 0.06 g of product per gram of catalyst per hour or greater, under more preferred conditions a productivity of 0.10 g of product per gram of catalyst per hour, and under most preferred conditions 0.25 g of product per gram of catalyst per hour or greater. The process of this invention results in selectivities toward α-unsubstituted acrylate ester of 70 percent or greater, under preferred conditions, of 80 percent or greater, and under most preferred conditions 85 percent or greater.

Conversions refer herein to the amount of haloalkane converted to products. Selectivities refer herein to the percentage of acrylate esters in the products prepared.

SPECIFIC EMBODIMENTS

The following examples are included for illustrative purposes only, and do not limit the scope of the invention or the claims. Unless otherwise specified, all parts and percentages are by weight.

EXAMPLE 1

A reactor is loaded with a 3 percent palladium on alumina catalyst. The catalyst is activated by flowing hydrogen at temperatures of about 275° C. over the catalyst for a period of 2 hours. After the reactor is cooled, the feed comprising carbon monoxide, methanol and 2-chloropropene is started. The ratio of methanol to 2-chloropropene is 2:1. The reaction temperature is 218° C. and the pressure is 600 psi. The flow rate of carbon monoxide is 150 GHSV (Gas Hourly Space Velocity), and the feed rate of the methanol and chloropropene mixture is 0.72 LHSV (Liquid Hourly Space Velocity). After 6 hours of continuous operation, the conversion of 2-chloropropene to methylmethacrylate was 73 percent. After 29 hours and after 50 hours, the conversion of 2-chloropropene to methylmethacrylate was 60 percent.

EXAMPLE 2

After 50 hours of continuous operation of the reactor described in Example 1, the temperature was increased to 290° C. Two hours after the increase in temperature, the conversion of 2-chloropropene to methylmethacrylate fell to 16 percent and continued to decrease rapidly with time. This example demonstrates that temperatures above 250° C. result in very poor conversions.

EXAMPLE 3

A reactor is loaded with a 3 percent palladium on alumina catalyst, which is activated in the method described in Example 1. Thereafter, a feed of methanol, 2-chloropropene and carbon monoxide is started and flowed over the catalyst. The ratio of methanol to 2-chloropropene in the feed is 1:1. The flow rate of the methanol and 2-chloropropene mixture is 0.72 LHSV. The flow rate of the carbon monoxide is 150 GHSV. The reaction temperature is 290° C. and the pressure is 600 psi. After 5 hours of continuous operation, the conversion of 2-chloropropene to methylmethacrylate is less than 1 percent.

EXAMPLE 4

A reactor is loaded with a 5 percent palladium on alumina catalyst. The catalyst is activated in flowing hydrogen at temperatures of about 275° C. for 2 hours. Thereafter, a feed of methanol, 2-chloropropene and carbon monoxide is fed to the reactor and flowed over the catalyst. The mole ratio of methanol to 2-chloropropene is 1:1. The feed rate of methanol and 2-chloropropene is 0.72 LHSV, while the feed rate of carbon monoxide is 150 GHSV. The reaction temperature is 253° C. and the pressure is 600 psi. After 25 hours of continuous operation, the conversion of 2-chloropropene to methylmethacrylate is only 3 percent.

EXAMPLE 5

A reactor is loaded with a 5 percent palladium on alumina catalyst. The catalyst is activated by flowing hydrogen gas over the catalyst at 275° C. for about 2.0 hours. A feed of methanol, 2-chloropropene and carbon monoxide is passed over the catalyst. The methanol to 2-chloropropene mole ratio is 2:1. The flow rate of the methanol and 2-chloropropene mixture is 0.72 LHSV, while the flow rate of the carbon monoxide is 150 GHSV. The temperature used is 207° C. and the pressure is 600 psi. The conversion of 2-chloropropene to methylmethacrylate is 46 percent, measured after 24 hours.

EXAMPLE 6

To a reactor is loaded a 3 percent palladium on alumina catalyst. The catalyst is activated in flowing hydrogen at temperatures of about 275° C. A feed of methanol, 2-chloropropene and carbon monoxide is passed over the catalyst, wherein the mole ratio of methanol to 2-chloropropene is 1:1. The flow rate of the methanol and 2-chloropropene mixture is 0.72 LHSV, while the flow rate of the carbon monoxide is 150 GHSV. The reaction temperature is 222° C. and the pressure is 600 psi. After 6 hours, the conversion of 2-chloropropene to methylmethacrylate is 20 percent and after 34 hours the conversion of 2-chloropropene to methylmethacrylate is 12 percent.

EXAMPLE 7

A reactor is loaded with 5 percent palladium on alumina catalyst. The catalyst is activated in flowing carbon monoxide at 250° C. and then the reactor is cooled. A feed of methanol, 2-choropropene and carbon monoxide, wherein the methanol to 2-chloropropene ratio is 2:1, is passed over the catalyst. The reaction temperature is 210° C. and the pressure is 600 psi. After 3 hours, the conversion of 2-chloropropene to methylmethacrylate is 7 percent and remains at this level even after 45 hours.

EXAMPLE 8

A reactor is loaded with a 5 percent palladium on alumina catalyst. The catalyst is activated in flowing hydrogen at 450° C. A feed of methanol, 2-chloropropene and carbon monoxide, wherein the ratio of methanol to 2-chloropropene is 2:1, is passed over the catalyst. After 5 hours of continuous operation at 210° C. and 600 psi the conversion of 2-chloropropene to methylmethacrylate is only 5 percent.

EXAMPLE 9

A sample of 5 percent palladium on alumina catalyst is reduced in flowing hydrogen at 450° C. The catalyst is cooled to room temperature and then slowly oxidized in the presence of oxygen at temperatures as high as 300° C. and cooled to room temperature. The catalyst is loaded into a reactor and activated in flowing hydrogen at 250° C. A feed of methanol, 2-chloropropene and carbon monoxide is passed over the catalyst, wherein the methanol to 2-chloropropene ratio is 2:1. The reaction temperature is 209° C. and the pressure is 600 psi. The conversion of 2-chloropropene to methylmethacrylate is 3 percent after 24 hours of continuous operation.

Table I compares the conditions and results of Examples 1–9.

TABLE I

| Example | % Palladium | Activation | Activation Temp °C. | Methanol/ 2-chloropropene | M/2-CP[1] Temp °C. | Results Time (hr) | Results % Conversion |
|---|---|---|---|---|---|---|---|
| 1 | 3 | $H^2$ | 275 | 2 | 218 | 6 | 73 |
|   |   |   |   |   |     | 29 | 60 |
|   |   |   |   |   |     | 50 | 60 |
| 2 | 3 | $H_2$ | 275 | 2 | 290 | 2 | 16 |
| 3 | 3 | $H_2$ | 275 | 1 | 290 | 5 | <1 |
| 4 | 5 | $H_2$ | 275 | 1 | 253 | 25 | 3 |
| 5 | 5 | $H_2$ | 275 | 2 | 207 | 24 | 46 |
| 6 | 3 | $H_2$ | 275 | 1 | 222 | 6 | 20 |
|   |   |   |   |   |     | 34 | 12 |
| 7 | 5 | CO | 250 | 2 | 210 | 3 | 7 |
|   |   |   |   |   |     | 45 | 7 |
| 8 | 5 | $H_2$ | 450 | 2 | 210 | 5 | 5 |
| 9 | 5 | * | * | 2 | 209 | 24 | 3 |

[1]M/2-CP = methanol/2-chloropropene
*The catalyst was activated at 450° C. in $H_2$, thereafter oxidized, and then activated at 275° C. in $H_2$.

A comparison of Examples 1 and 6 demonstrates that the use of a ratio of methanol to 2-chloropropene of 1:1 gives significantly lower conversion than the use of a methanol to 2-chloropropene ratio of 2:1. Example 2 demonstrates that the use of temperatures in the vicinity of 290° C. results in a significantly lower conversion after 2 hours. A comparison of Examples 5 and 7 demonstrates that the use of hydrogen gas to reduce the catalyst results in a higher conversion than the use of carbon monoxide to reduce the catalyst.

Comparison of Examples 5 and 8 demonstrates that the use of higher temperatures in the activation of the catalyst results in a significantly lower conversion when the catalyst is used in the carbonylation reaction.

What is claimed is:

1. A vapor phase process for the preparation of an α-substituted acrylate ester which comprises contacting (a) a haloalkene, wherein the halogen is substituted on an olefinic carbon atom which is further substituted with a $C_{1-10}$ alkyl, $C_{3-10}$ cycloalkyl, $C_{6-10}$ aryl, $C_{7-10}$ alkaryl, $C_{7-10}$ aralkyl, cyano, or trihalomethyl group; (b) an alcohol or an ether; and (c) carbon monoxide in the presence of a heterogeneous catalyst which comprises palladium, platinum, nickel, ruthenium or rhodium, on a support, wherein the catalyst has a metal dispersion of between about 50 and 95 percent, under conditions such that an α-substituted acrylate ester and a hydrocarbyl halide is prepared wherein the catalyst productivity is 0.06 g of product per gram of catalyst per hour or greater; wherein the catalyst is impregnated by incipient wetness by heating the support to a temperature of between about 75° C.-150° C. and contacting the support with a sufficient amount of an aqueous hydrochloric acid solution of a palladium, platinum, nickel, ruthenium or rhodium salt with a pH of about 3.0 or lower to provide the desired loading and dispersion, wherein the aqueous solution is at a temperature of between about 50° C.95° C. at the time of contacting; and the catalyst is activated by hydrogen gas over the catalyst at a temperature of between about 150° C.-350° C. for a period of time sufficient to reduce a significant amount of the metal salt on the support.

2. The process of claim 1 wherein the haloalkene corresponds to the formula

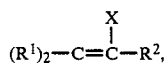

the alcohol corresponds to the formula $R^3$—OH, the ether corresponds to one of the formulas $R^3$—O—$R^3$,

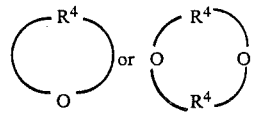

the acrylate ester corresponds to one of the formulas

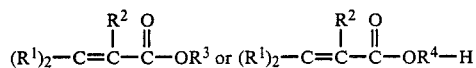

and the hydrocarbyl halide corresponds to the formula $R^1X$ wherein $R^1$ is hydrogen, $C_{1-10}$ alkyl, $C_{6-10}$ aryl, $C_{3-10}$ cycloalkyl, $C_{7-10}$ alkaryl, $C_{7-10}$ aralkyl, substituted $C_{1-10}$ alkyl, substituted $C_{6-10}$ aryl, substituted $C_{3-10}$ cycloalkyl, substituted $C_{7-10}$ alkaryl or substituted $C_{7-10}$ aralkyl, wherein the substituent is a nitro, cyano, carbonyloxyhydrocarbyl, formyl, amino, hydroxyl, amido or halo group;

$R^2$ is $C_{1-10}$ alkyl, $C_{3-10}$ cycloalkyl, $C_{6-10}$ aryl, $C_{7-10}$ alkaryl or $C_{7-10}$ aralkyl;

$R^3$ is $C_{1-10}$ alkyl, $C_{3-10}$ cycloalkyl, $C_{6-10}$ aryl, $C_{7-10}$ alkaryl or $C_{7-10}$ aralkyl;

$R^4$ is a hydrocarbylene radical; and

X is halogen.

3. The process of claim 2 wherein the ether corresponds to the formula $R^3$—O—$R^3$ and the α-unsubstituted acrylate ester corresponds to the formula

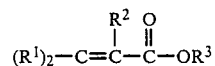

wherein $R^1$ is hydrogen, $C_{1-10}$ alkyl, $C_{6-10}$ aryl, $C_{3-10}$ cycloalkyl, $C_{7-10}$ alkaryl, $C_{7-10}$ aralkyl, substituted $C_{1-10}$ alkyl, substituted $C_{6-10}$ aryl, substituted $C_{3-10}$ cycloalkyl, substituted $C_{7-10}$ alkaryl or substituted $C_{7-10}$ aralkyl, wherein the substituent is a nitro, cyano, carbonyloxyhydrocarbyl, formyl, amino, hydroxyl, amido or halo group;

$R^2$ is $C_{1-10}$ alkyl, $C_{3-10}$ cycloalkyl, $C_{6-10}$ aryl, $C_{7-10}$ alkaryl or $C_{7-10}$ aralkyl; and $R^3$ is $C_{1-10}$ alkyl, $C_{3-10}$ cycloalkyl, $C_{6-10}$ aryl, $C_{7-10}$ alkaryl or $C_{7-10}$ aralkyl.

4. The process of claim 3 wherein the mole ratio of alcohol or ether to haloalkene is 1.5 or greater.

5. The process of claim 4 wherein the mole ratio of alcohol or ether to haloalkene is 2.0 or greater.

6. The process of claim 4 wherein the catalyst is prepared by impregnating a support with a metal halide.

7. The process of claim 6 wherein the metal is nickel or palladium.

8. The process of claim 7 wherein the metal is palladium.

9. The process of claim 8 wherein the haloalkene, carbon monoxide and alcohol or ether are contacted at a temperature of between about 125° C. and 250° C.

10. The process of claim 9 wherein the haloalkene, carbon monoxide and alcohol or ether are contacted at a temperature of between about 170° C. and 240° C.

11. The process of claim 9 wherein the pressure is between about 100 and 800 psi.

12. The process of claim 11 wherein the pressure is between about 300 and 600 psi.

13. The process of claim 11 wherein the catalyst support is alumina, activated carbon, silica, a silica-alumina zeolitic molecular sieve, titanium oxide, niobium oxide, lanthanum oxide, thorium oxide or silicon carbide.

14. The process of claim 13 wherein the support is alumina activated carbon, silica, or an aluminosilicate zeolitic molecular sieve.

15. The process of claim 13 wherein the support is alumina, activated carbon or silica.

16. The process of claim 15 wherein the support is alumina.

17. The process of claim 15 wherein the catalyst contains between about 0.1 and 10 percent by weight of metal.

18. The process of claim 17 wherein $R^1$ is hydrogen or $C_{1-10}$ alkyl; $R^2$ is $C_{1-10}$ alkyl; $R^3$ is $C_{1-10}$ alkyl; and X is chlorine or bromine.

19. The process of claim 18 wherein $R^1$ is hydrogen or $C_{1-5}$ alkyl; $R^2$ is $C_{1-5}$ alkyl; $R^3$ is $C_{1-5}$ alkyl; and X is chlorine.

20. The process of claim 19 wherein $R^1$ is hydrogen; $R^2$ is methyl; and $R^3$ is methyl.

21. A vapor phase process for the preparation of methylmethacrylate which comprises contacting carbon monoxide, methanol or dimethyl ether and 2-chloropropene in the vapor phase in the presence of a palladium on alumina catalyst with a palladium dispersion of between about 50 and 90 percent, and the methanol to 2-chloropropene mole ratio is 2:1 or greater, under conditions such that methylmethacrylate and methyl chloride are prepared and the catalyst productivity is 0.06 g of product per gram of catalyst per hour wherein the catalyst is impregnated by incipient wetness by heating the support to a temperature of between about 75° C.–150° C. and contacting the support with a sufficient amount of an aqueous hydrochloric acid solution of a palladium salt with a pH of about 3.0 or lower to provide the desired loading and dispersion, wherein the aqueous solution is at a temperature of between about 50° C.–95° C. at the time of contacting; and the catalyst is activated by passing hydrogen over the palladium salt impregnated on alumina at a temperature of between about 150° C.–350° C. for a period of time sufficient to reduce a significant amount of the metal salt on the support.

22. The process of claim 21 wherein the catalyst is activated prior to the contacting by passing hydrogen gas over the catalyst at a temperature of between 150° C. and 350° C. for about 1 to 10 hours.

23. The process of claim 22 wherein the methanol, 2-chloropropene and carbon monoxide are contacted at a temperature of between about 125° C. and 250° C.

24. The process of claim 23 wherein the pressure is between about 100 and 800 psi.

25. The process of claim 24 wherein the catalyst comprises between about 0.1 and 10.0 percent by weight of palladium on alumina.

* * * * *

UNITED STATES PATENT AND TRADEMARK OFFICE
CERTIFICATE OF CORRECTION

PATENT NO.　: 　4,743,705
DATED　　　: 　May 10, 1988
INVENTOR(S) : 　Dennis A. Hucul; Kathryn A. Eickholt It is certified that error appears in the above-identified patent and that said Letters Patent is hereby corrected as shown below:

On cover sheet, in OTHER PUBLICATIONS, "Catalysts" has been misspelled;

On cover sheet, in the ABSTRACT, "a-substituted" at lines 2 and 10, should be -- α-substituted --;

Col. 2, lines 1-4, delete "[HCl]";

Col. 4, line 60, delete "$R^4Y-X$" and insert -- $R^4H-X$ --;

Col. 5, line 48, delete "[hydrogen or]";

Col. 6, line 18, insert a comma after the word "rhodium";

Col. 11, line 57, insert a hyphen after "50°C.".

Signed and Sealed this

Seventh Day of February, 1989

*Attest:*

DONALD J. QUIGG

*Attesting Officer*　　　　*Commissioner of Patents and Trademarks*